United States Patent
Norton et al.

(10) Patent No.: US 9,687,271 B2
(45) Date of Patent: Jun. 27, 2017

(54) UNIPORT HAVING A ONE-PIECE BODY ANCHOR AND AN ELONGATED SURGICAL INSTRUMENT PASSAGEWAY FOR USE IN SINGLE SITE SURGICAL PROCEDURES

(71) Applicant: Axcess Instruments, Inc., Tyler, TX (US)

(72) Inventors: Michael J. Norton, Tyler, TX (US); Noel D. Ischy, Tyler, TX (US)

(73) Assignee: Axcess Instruments, Inc., Tyler, TX (US)

( * ) Notice: Subject to any disclaimer, the term of this patent is extended or adjusted under 35 U.S.C. 154(b) by 238 days.

(21) Appl. No.: 14/688,738

(22) Filed: Apr. 16, 2015

(65) Prior Publication Data

US 2015/0216562 A1    Aug. 6, 2015

Related U.S. Application Data

(63) Continuation-in-part of application No. 11/710,388, filed on Feb. 23, 2007, and a continuation-in-part of application No. 12/220,248, filed on Jul. 23, 2008, now Pat. No. 9,011,319.

(51) Int. Cl.
*A61B 17/34* (2006.01)
*A61B 17/02* (2006.01)

(52) U.S. Cl.
CPC ...... *A61B 17/3423* (2013.01); *A61B 17/0218* (2013.01); *A61B 2017/3429* (2013.01); *A61B 2017/3445* (2013.01); *A61B 2017/3447* (2013.01); *A61B 2017/3466* (2013.01); *A61B 2017/3482* (2013.01); *A61B 2017/3492* (2013.01)

(58) Field of Classification Search
CPC ........ A61B 17/3421; A61B 2017/3492; A61B 2017/3447; A61B 2017/3445; A61B 2017/3425; A61B 2017/00278; A61B 17/3431; A61B 17/3474; A61B 2017/3419; A61B 2017/3484

See application file for complete search history.

(56) References Cited

U.S. PATENT DOCUMENTS

| | | |
|---|---|---|
| 4,016,884 A | 4/1977 | Kwan-Gett |
| 4,306,545 A | 12/1981 | Ivan et al. |
| 4,402,683 A | 9/1983 | Kopman |
| 4,895,561 A | 1/1990 | Mahurkar |
| 5,183,471 A | 2/1993 | Wilk |
| 5,269,772 A | 12/1993 | Wilk |
| 5,507,758 A | 4/1996 | Thomason et al. |

(Continued)

*Primary Examiner* — Katrina Stransky
(74) *Attorney, Agent, or Firm* — Locke Lord LLP; Scott D. Wofsy; Arpita G. Buesing

(57) ABSTRACT

One aspect provides a multiple access body uniport for performing single site surgery on a body that comprises a one-piece body anchor defined by a longitudinal length and an uppermost surface and a lowermost surface. The uniport includes at least two surgical instrument passageways located through the one-piece body anchor and terminate at an entrance aperture on the uppermost surface and at an exit aperture on the lowermost surface, and also includes at least a third surgical instrument passageway located through the one-piece body anchor and having an elongated access opening extending across a portion of the uppermost surface and having an exit aperture on the lowermost surface.

15 Claims, 4 Drawing Sheets

(56) References Cited

U.S. PATENT DOCUMENTS

| | | | |
|---|---|---|---|
| 5,569,205 A | | 10/1996 | Hart et al. |
| 6,066,090 A | | 5/2000 | Yoon |
| 6,086,603 A | * | 7/2000 | Termin ............... A61B 17/3421 |
| | | | 604/164.01 |
| 6,277,064 B1 | | 8/2001 | Yoon |
| 6,440,061 B1 | | 8/2002 | Wenner et al. |
| 6,454,783 B1 | | 9/2002 | Piskun |
| 6,508,759 B1 | | 1/2003 | Taylor et al. |
| 6,551,270 B1 | | 4/2003 | Bimbo et al. |
| 6,648,816 B2 | | 11/2003 | Irion et al. |
| 6,669,674 B1 | | 12/2003 | Macoviak et al. |
| 6,916,331 B2 | | 7/2005 | Mollenauer et al. |
| 7,753,901 B2 | | 7/2010 | Piskun et al. |
| 9,017,250 B2 | | 4/2015 | Okoniewski |
| 2003/0004520 A1 | | 1/2003 | Haarala et al. |
| 2003/0028179 A1 | * | 2/2003 | Piskun ................... A61B 90/50 |
| | | | 606/1 |
| 2004/0167543 A1 | | 8/2004 | Mazzocchi et al. |
| 2005/0137609 A1 | | 6/2005 | Guiraudon |
| 2005/0251144 A1 | * | 11/2005 | Wilson ................... A61B 5/031 |
| | | | 606/108 |
| 2006/0020241 A1 | | 1/2006 | Piskun et al. |
| 2007/0049966 A1 | | 3/2007 | Bonadio et al. |
| 2007/0208312 A1 | | 9/2007 | Norton et al. |
| 2009/0012477 A1 | | 1/2009 | Norton et al. |
| 2011/0082343 A1 | * | 4/2011 | Okoniewski ....... A61B 17/3423 |
| | | | 600/208 |

* cited by examiner

UNIPORT HAVING A ONE-PIECE BODY ANCHOR AND AN ELONGATED SURGICAL INSTRUMENT PASSAGEWAY FOR USE IN SINGLE SITE SURGICAL PROCEDURES

CROSS-REFERENCE TO RELATED APPLICATION

This application is a continuation in part of U.S. patent application Ser. No. 11/710,388, filed Feb. 23, 2007, and published as U.S. Publication No. 2007/0208312, entitled "Apparatus and Method of Minimally Invasive Surgery," and U.S. patent application Ser. No. 12/220,248, filed Jul. 23, 2008, and published as U.S. Publication No. 2009/0012477, entitled "Conical Laparoscopic Apparatus For Minimally Invasive Surgery," both of which are incorporated herein by reference in their entirety.

TECHNICAL FIELD

This application is directed to a multiple access one-piece uniport having an elongated surgical instrument passageway for performing single site surgery on a body.

BACKGROUND

Minimally invasive surgery has improved patient care by decreasing pain, shortening hospital stays, offering a faster recovery time and much smaller scars. In fact, the surgical procedure can be much shorter than standard procedures and offers less chance of infection and other associated problems. In addition, the advent of robotic assisted surgery has further enhanced these benefits in certain specific operations. As such, laparoscopic procedures, whether done manually by a surgeon or with the assistance of robotics, are improving patient care.

During laparoscopic procedures for abdominal surgeries, the surgeon makes a series of three to five small, dime-sized incisions in the patient's abdomen. Carbon dioxide gas is used to inflate the abdomen and create a working space between the internal organs and the skin. A rigid camera, or scope, is placed in one of the incisions, providing the surgeon with a magnified view of the patient's internal organs on a television monitor in the operating room. In some procedures, such as laparoscopic colon procedures, a slightly larger incision may be needed to remove the colon specimen.

Thus, the procedure requires body access devices, which are utilized to introduce visualization equipment and operative instruments rather than a standard incision to access a specific organ system.

In the past, devices with multiple parallel channels were not able to achieve sufficient triangulation for many operation to be performed. Unfortunately, the narrow parallel channels in these devices limited the field of view and reduced depth perception, and thus, did not met the broad needs of the surgical community.

SUMMARY

One aspect provides a multiple access body uniport for performing single site surgery on a body that comprises a one-piece body anchor defined by a longitudinal length and an uppermost surface and a lowermost surface. This embodiment includes at least two surgical instrument passageways located through the one-piece body anchor and terminate at an entrance aperture on the uppermost surface and at an exit aperture on the lowermost surface, and also includes at least a third surgical instrument passageway located through the one-piece body anchor and having an elongated access opening extending across a portion of the uppermost surface and having an exit aperture on the lowermost surface.

BRIEF DESCRIPTION

Reference is now made to the following descriptions taken in conjunction with the accompanying drawings, in which.

Figure 3:
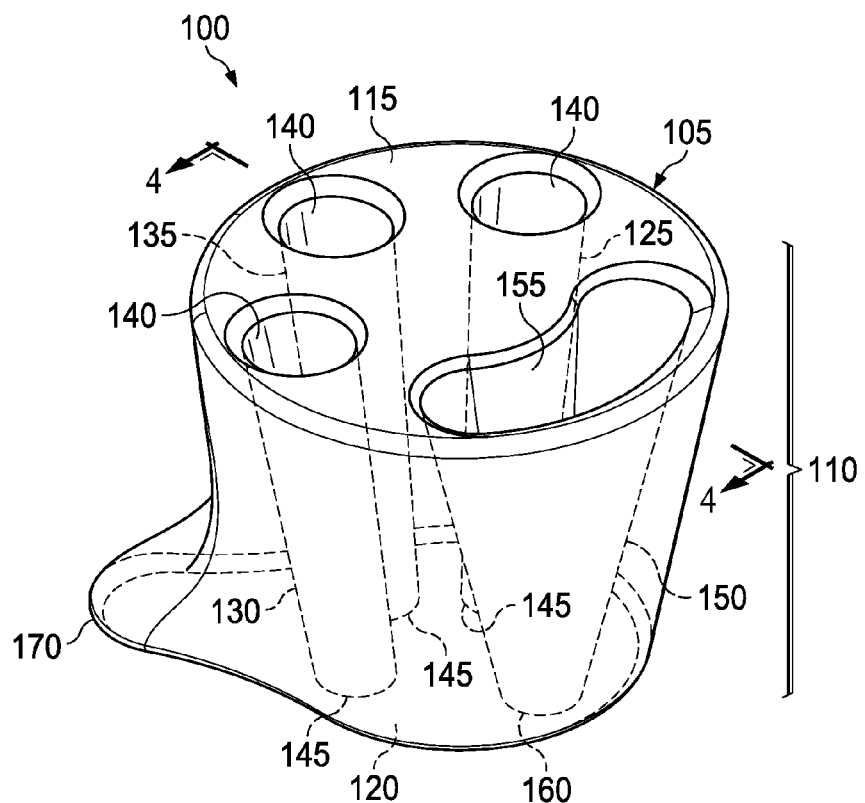
FIG. 3 is a perspective view of another embodiment of a uniport having a one-piece body anchor, an elongated surgical instrument passageway and an anchor stabilizer.
Figure 4:
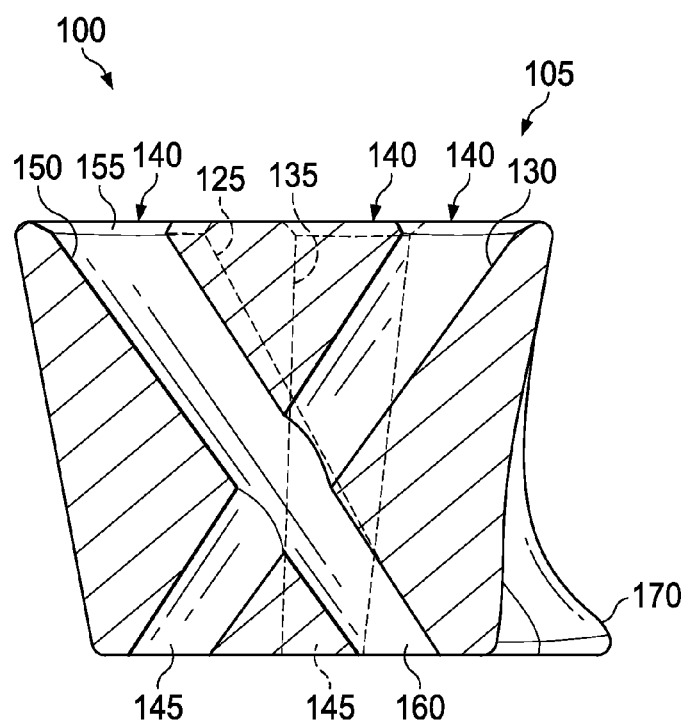
Figure 5:
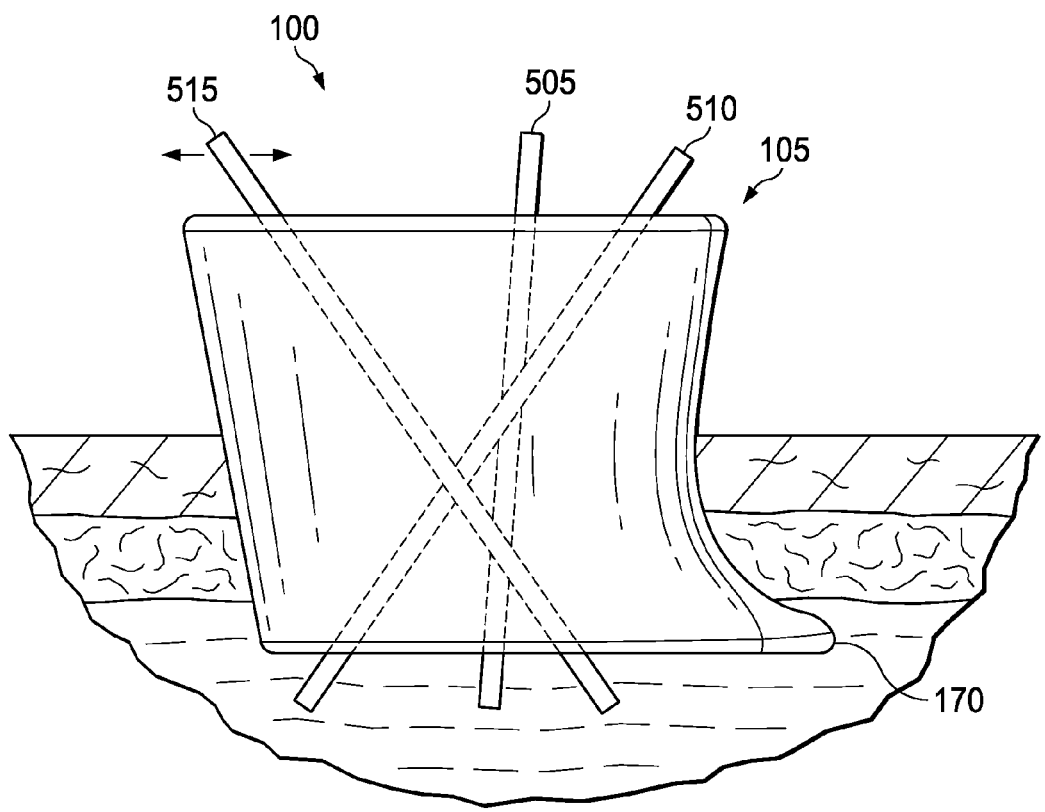

FIG. 4 is a perspective view of the uniport of FIB. 3 having a one-piece body anchor and an elongated surgical instrument passageway and the anchor stabilizer and in which at least two other surgical instrument passageways cross within the one-piece body anchor; and FIG. 5 is a perspective view of the uniport of FIG. 3 positioned within an operative body, illustrating possible placements of surgical instrument through the elongated surgical instrument passageway and at least two other surgical instrument passageways.

DETAILED DESCRIPTION

The various embodiments of the present disclosure provide a multiple access body uniport that has a surgical instrument passageway with an elongated access opening extending across a portion of the uppermost surface of the uniport for performing single site surgery on a body. The elongated opening allows the operative field to be increased in a specific area or direction that enhances retraction and provides improved function of the core device instrument channels. These embodiments allow a surgeon to introduce numerous types of instruments with triangulation through one body access opening. The embodiments disclosed herein preserve triangulation and create the required field and depth of view, while allowing a surgeon to utilize one, small uniport for multiple simultaneous tasks required to complete an operation on any applicable body area or space.

Single site surgery, as that term is used herein and in the claims, is a relatively new surgical method allowing multiple instrumentation to be placed through a single access device, thus requiring only one incision in contrast to multiple incisions typically required by convention laparoscopic procedures. Utilizing a new algorithm, the instrumentation then must provide a separation of the operative field with instruments originating from the single site access device. The specific single site operation is then performed. Optics for viewing must be accommodating to allow for recognition of the 3 dimensional field of the operation.

Figure 1A:
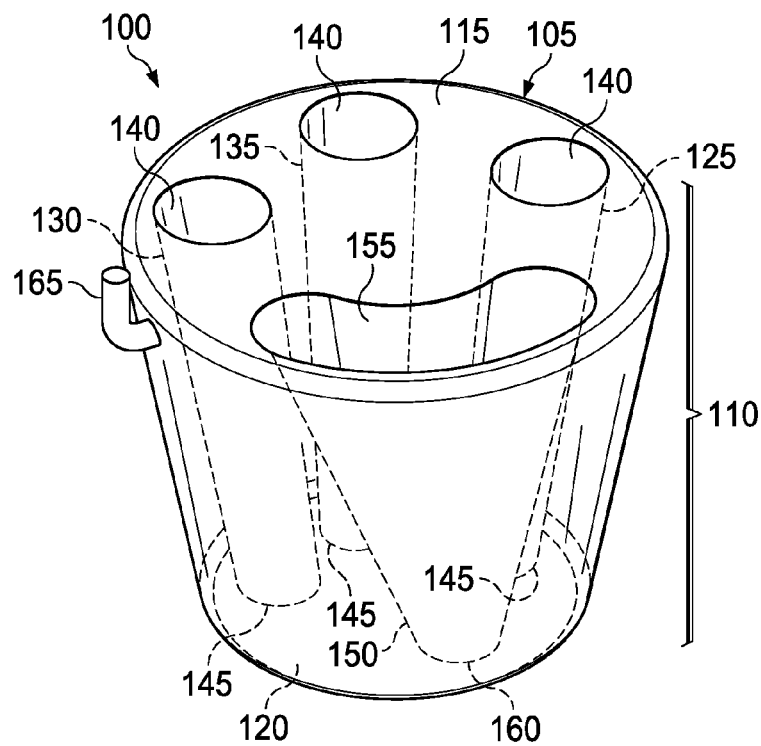
FIG. 1A is a perspective view of one embodiment of a uniport having a one-piece body anchor and an elongated surgical instrument passageway.
Figure 1B:
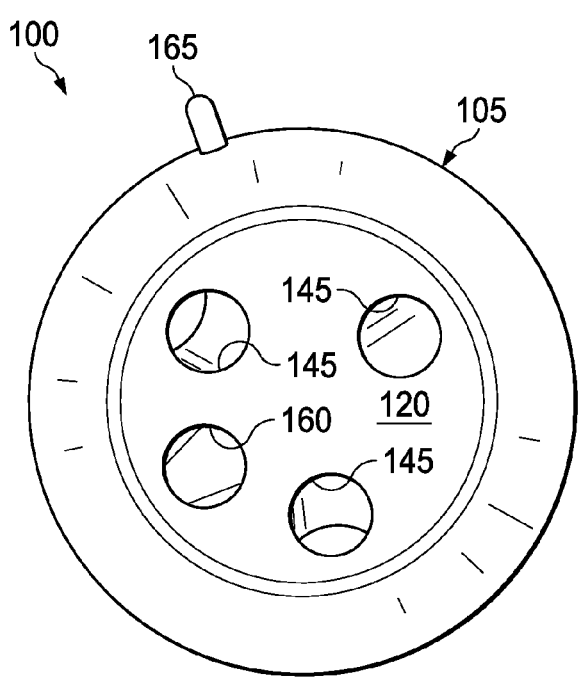
FIG. 1B is a bottom view of the uniport of FIG. 1A.

FIG. 1A illustrates a perspective view of one embodiment of a uniport 100 as provided by this disclosure and FIG. 1B illustrates a bottom view of FIG. 1A. In this embodiment, the uniport 100 comprises one-piece body anchor 105 having a longitudinal length 110, an uppermost surface 115, and a lowermost surface 120. As used herein and in the claims, the one-piece body anchor 105 is an anchor/surgical access device that provides both the anchoring function and the surgical instrument passageways all of which are physically and integrally incorporated into the one-piece body anchor 105. During a surgical procedure, the surgeon inserts the one-piece body anchor 105 into a small incision made in the body and anchors the body anchor 105 to the operative body by suturing it in place. The surgeon then gains access to the interior of the body by inserting surgical instruments into surgical instrument passageways that extend through the one-piece body anchor 105. In one embodiment, the uniport 100 has a conical shape that tapers from the top to the bottom of the device. Though the illustrated embodiment has a round conical shape, it also may be other rounded shapes, such as oval or elliptical shapes.

The material from which the one-piece body anchor 105 is constructed or formed may comprise various types of materials. For example, the one-piece body anchor 105 may be comprised of a solid material. As used herein and in the claims, a solid material is a material that holds its shape at normal room temperatures (~72° F.) and has sufficient rigidity to allow it to be used as a body anchor and entry port for surgical instruments and is not a gas or a liquid at room temperatures. However, in certain embodiments as explained below, a gas, liquid, or a gel may be injected into the one-piece body anchor 105 to cause it to become sufficiently rigid to be used as a body anchor and entry port for surgical instruments. Some non-exhaustive examples of a solid material include glass, metal, a semi-rigid or moldable gel (which is one that holds its shape to meet the above-stated use requirements), rubber (including natural occurring rubber or a compound of rubber), different types of plastics, such as those made from organic or inorganic resin compounds. One may use conventional fabrication techniques, such as machining or injectable mold processes, to form or shape the above-materials into the uniport 100. In another embodiment, the uniport 100 is manufactured in a way such that it or a portion of it can be inflated to obtain the degree of rigidity for it to meet the above-stated use requirement. For example, in such embodiments, a manufacturer may use an injection process to inject a thin elastic plastic material into a mold to obtain the appropriate general deflated shape. This manufacturing process would include the incorporation of inflation valves into the uniport's body to allow a surgeon to fill it or a portion of it with a gas, gel, or liquid to obtain its general operative forms as illustrated in the various embodiments discussed herein.

Figure 2A:
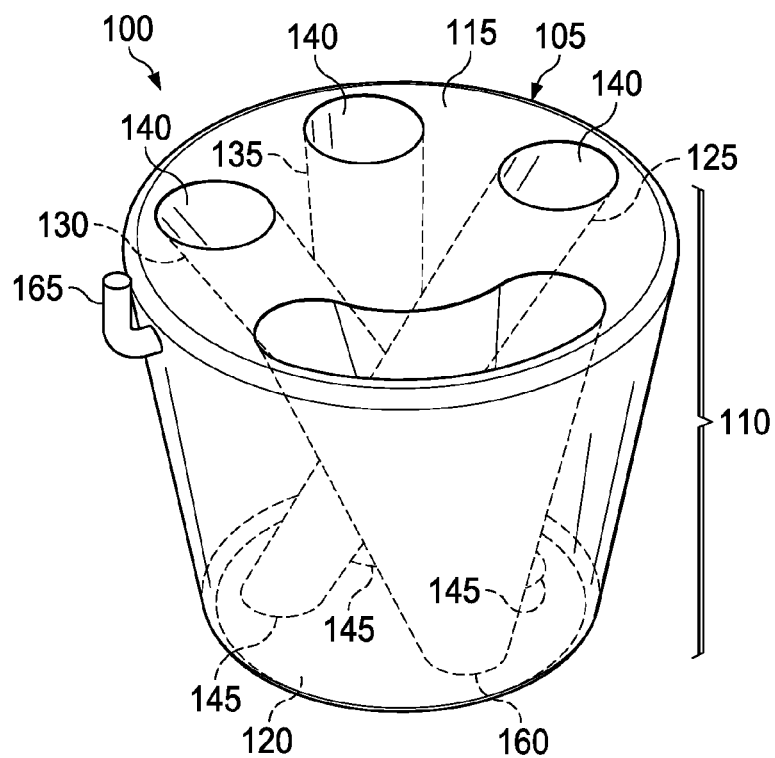
FIG. 2A is a perspective view of another embodiment of a uniport having a one-piece body anchor and an elongated surgical instrument passageway in which at least two other surgical instrument passageways cross within the one-piece body anchor.
Figure 2B:
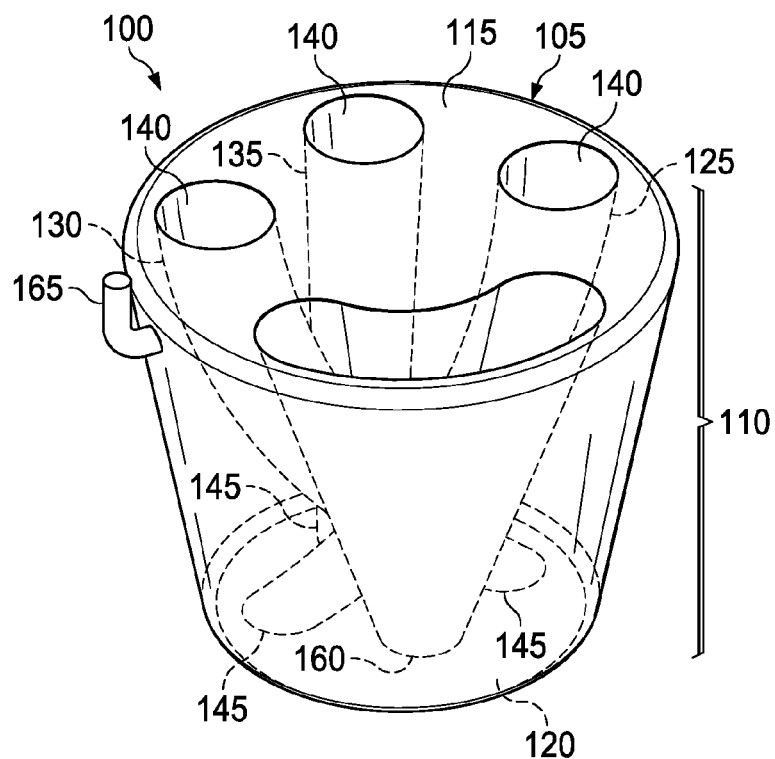
FIG. 2B is a perspective view of another embodiment of a uniport having a one-piece body anchor and an elongated curgical instrument passageway in which at least one or more of the other surgical instrument passageways are curved in a converging manner.

The one-piece body anchor 105 further includes at least two surgical instrument passageways 125, 130, or 135 that are located through the one-piece body anchor 105 and that terminate at entrance apertures 140 on the uppermost surface 115 and at exit apertures 145 on the lowermost surface 120. One or more of the surgical instrument passageways 125, 130, or 135 may be straight or curved or any combination thereof. Additionally, the surgical instrument passageways are structural components of the one-piece body anchor 105 and are present even when a surgical instrument is not inserted into the one-piece body anchor 105. In one embodiment, two or more of the surgical instrument passageways 125, 130, or 135 may cross each other within the one-piece body anchor 105 but without physically intersecting each other, as shown in FIGS. 2A and 2B. This crisscrossing feature provides an added advantage of providing improved triangulation during surgery. However, in other embodiments, the surgical instrument passageways 125, 130, or 135 may not cross each other within the one-piece body anchor 105, as seen in the embodiment of FIG. 1A. In an alternative embodiment, the surgical instrument passageways 125, 130, or 135 may converge toward one another with or without crossing each other within the one-piece body anchor 105.

In those embodiments where the one-piece body anchor 105 comprises a solid material, as defined above, the surgical instrument passageways 125, 130, or 135 may be formed by machining or drilling the one-piece anchor 105 to remove the solid material from the one-piece body anchor 105 to form the surgical instrument passageways 125, 130, or 135. In alternative embodiments, the surgical instrument passageways 125, 130, or 135, may be formed by way of an injection molding processes that injects a material into an injection mold such that the surgical instrument passageways 125, 130, or 135, are formed by the voids within the injection mold.

In certain embodiments, the entrance apertures 140 may have a conical shape that provides more movement and manipulation of surgical instruments when inserted through surgical instrument passageways 125, 130, or 135. Though the surgical instruments are not shown, it should be understood that the surgical instrument passageways 125, 130, or 135 could accommodate various types of conventional, surgical instruments used during various types and stages of laparoscopic surgery, including those used in surgical robotics procedures.

The uniport 100 further includes at least a unique, third surgical instrument passageway 150 located through the one-piece body anchor 105. The third or elongated surgical instrument passageway 150 has an elongated access opening 155 extending across a portion of the uppermost surface 115 and has an exit aperture 160 on the lowermost surface 120. As used herein and in the claims, an elongated access opening is an opening that has a length that is greater than its width. In one embodiment, the length is at least two times longer than its width, and in another embodiment, the length is at least three times larger than the width. The surgical instrument passageway 150 allows for maintenance of spatial relationship with the other surgical instrument passageway 125, 130, or 135 so the surgeon can easily exchange surgical instruments without losing relationship within the instrument grouping. In one embodiment, the length of the third surgical instrument passageway 150 narrows as it extends through the one-piece body anchor 105 from the uppermost surface 115 to the lowermost surface. In such embodiments, the third elongated surgical instrument passageway 150 has a conical shape that tapers from the uppermost surface 115 to the lowermost surface 120. Surgical instrument passageways 125, 130, 135 and 150 include conventional seals within the passageways that serve to retain the body inflation gas while various instruments are inserted and withdrawn through the uniport 100 during the operation.

Various embodiments of the uniport 100 may also include a tie down post 165, which may also be a notch formed in the one-piece body anchor 105. The tie down post 165, or notch, provides a point about which a surgeon can anchor or tie down and secure the uniport 100 to the operative body.

The uniport's 100 overall configuration allows for rotation within the incision and the elongated access opening 150 creates an outer working perimeter that can rotate around the inner core of instruments inserted through the various surgical instrument passageway 125, 130 or 135. The surgical instruments' ease of advancement or retraction into and out of the surgical instrument passageways 125, 130, or 135 optimize the working area of the uniport 100 and provides associated retraction. In addition, however, the elongated access opening 155 on the uppermost surface 115 allows for independent movement across the uppermost surface 115 of the uniport 100, which in turn, allows a surgical instrument to move away from the center point of the uniport 100. In one embodiment, the elongated access opening 155 is located adjacent and extends along an outermost edge of the one-piece body anchor 105. In one aspect of this embodiment, the elongated access opening 155 has an arcuate shape. A further advantage of the one-piece anchor 105 is that the elongated access opening 155 provides an increase in a specific area or direction of the operative field and provides greater operative field triangulation for improved surgical function.

FIG. 3 is a perspective view of another embodiment of the uniport 100. This embodiment is similar to the embodiment illustrated in FIG. 1, and as such, elements that are common with FIG. 1 are referenced the same. This embodiment, however, further includes a stabilizing anchor 170 that forms a portion of the one-piece body anchor 105. The stabilizing anchor 165 is laterally located at the lowermost exit surface 120 and has an upper surface 115 extending outwardly from the one-piece body anchor 105 and beyond a perimeter of the uppermost surface 115, as seen in FIG. 3. The geometric configuration of the stabilizing anchor 170 may vary within the physical description as just mentioned above. However, in one embodiment, the stabilizing anchor 170 has a general wedge or "V" shape and may have a curved or flat top and a flat, curved, or wedged-shaped bottom, and extends from one side of the one-piece body anchor 105. The stabilizing anchor 170 serves as a wedged guide that helps the surgeon to easily insert the uniport 100 into an incision and the operative body. Further, once the surgeon positions and sutures the uniport 100 in place, the stabilizing anchor 170 can serve as a pivot or fulcrum point within the body about which the surgeon can rotate or pivot the uniport 100 within the operative body. The benefits of the stabilizing anchor 170 are further enhanced by the presence of the elongated surgical instrument passageway 150. The combination of these two features provide the surgeon greater flexibility during a surgical procedure and allows the surgeon to achieve better triangulation of the surgical instruments within the operative body.

FIG. 4 is a sectional view of the embodiment illustrated in FIG. 3. This embodiment illustrates the crisscrossing of the various surgical instrument passageways 125, 130, or 135 and 150. As noted above, the crisscrossing offers an added advantage of providing improved triangulation during surgery, which is further enhanced by the presence of the stabilizing anchor 170 and the elongated surgical instrument passageway 150.

FIG. 5 illustrates the embodiment of FIG. 4 in which the uniport 100 is positioned with an operative body, such as a human's or animal's body, and also generally illustrates surgical instruments 505, 510 and 515 inserted through the above-discussed surgical instrument passageways 125, 130, and 150, respectively. The left and right arrows associated with surgical instrument 515 and inserted through elongated surgical passageway 150 generally illustrate the lateral movement of the surgical instrument 515 that is available within the elongated surgical instrument passageway 150.

Those skilled in the art to which this application relates will appreciate that other and further additions, deletions, substitutions and modifications may be made to the described embodiments.

What is claimed is:

1. A multiple access body uniport for performing single site surgery on a body, comprising:
 a one-piece body anchor defined by a longitudinal length and an uppermost surface and a lowermost surface, wherein:
  at least two surgical instrument passageways located through said one-piece body anchor terminate at an entrance aperture on said uppermost surface and at an exit aperture on said lowermost surface;
  at least a third surgical instrument passageway located through said one-piece body anchor and having an elongated access opening extending across a portion of said uppermost surface and having an exit aperture on said lowermost surface; and
  an anchor stabilizer laterally located at said lowermost exit surface and having an upper surface extending outwardly from said one-piece body anchor and beyond a perimeter of said uppermost surface.

2. The multiple access body uniport of claim 1 wherein said elongated access opening is located adjacent and extends along an outermost edge of said one-piece body anchor.

3. The multiple access body uniport of claim 2 wherein said elongated access opening is arcuate.

4. The multiple access body uniport of claim 1 wherein a length of said elongated access opening is at least two times longer than a width of said elongated access opening.

5. The multiple access body uniport of claim 4 wherein said length of said elongated access opening is at least three times larger than said width of said elongated access opening.

6. The multiple access body uniport of claim 1 wherein said at least two surgical instrument passageways cross one another within said one-piece body anchor.

7. The multiple access body uniport of claim 1 further including at least a fourth surgical instrument passageway that extends through said one-piece body anchor from said uppermost surface to said lowermost surface.

8. The multiple access body uniport of claim 1, wherein a length of said third surgical instrument passageway narrows as said third surgical instrument passageway extends from said uppermost surface to said lowermost surface.

9. The multiple access body uniport of claim 8 wherein said third elongated surgical instrument passageway has a conical shape that tapers from said uppermost surface to said lowermost surface.

10. The multiple access body uniport of claim 1 wherein said one-piece body anchor is comprised of a solid material.

11. The multiple access body uniport of claim 10, wherein said solid material is glass, metal, a semi-rigid gel, an organic resin compound or rubber.

12. The multiple access body uniport of claim 1, wherein said one-piece body anchor is comprised of an inflatable material.

13. The multiple access body uniport of claim 1 wherein said one-piece body anchor has a conical shape that tapers from said uppermost surface to said lowermost surface.

14. The multiple access body uniport of claim 1 wherein one or more of said at least two surgical instrument passageways or said at least a third surgical instrument passageway are curved.

15. The multiple access body uniport of claim 1 wherein at least two of said at least two surgical instrument passageways or said at least a third surgical instrument passageway converge toward one another without crossing each other with said one-piece body anchor.

* * * * *